US00PP28611P2

(12) United States Plant Patent
Sato et al.

(10) Patent No.: US PP28,611 P2
(45) Date of Patent: Nov. 7, 2017

(54) **NEW GUINEA *IMPATIENS* PLANT NAMED 'SAKIMP042'**

(50) Latin Name: ***Impatiens hybrida* hort**
Varietal Denomination: SAKIMP042

(71) Applicant: Sakata Seed Corporation, Yokohama (JP)

(72) Inventors: Chihiro Sato, Nagano (JP); Shinji Minemura, Nagano (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 14/999,104

(22) Filed: Mar. 30, 2016

(51) Int. Cl.
*A01H 5/02* (2006.01)

(52) U.S. Cl.
USPC ..... Plt./318.4

(58) Field of Classification Search
USPC ..... Plt./318.3, 318.4, 318.5
CPC ..... A01H 5/0261
See application file for complete search history.

*Primary Examiner* — Kent L Bell
(74) *Attorney, Agent, or Firm* — Barbara Campbell; Bethany R. Roahrig; Cochran Freund & Young, LLC

(57) ABSTRACT

An *Impatiens* plant particularly distinguished by having light coral-pink flowers, and green leaves, is disclosed.

2 Drawing Sheets

Genus and species: *Impatiens hybrida* hort.
Variety denomination: 'SAKIMP042'.

BACKGROUND OF THE NEW PLANT

The present invention comprises a new and distinct variety of New Guinea *Impatiens* plant, botanically known as *Impatiens hybrida* hort, and referred to by the variety name 'SAKIMP042'. The present *Impatiens* variety originated in Misato, Japan from an interspecific hybridization between the proprietary female *Impatiens* variety 'NE-5331' (unpatented) having salmon-orange flowers and the proprietary male *Impatiens* variety 'NJ-1174A' (unpatented) having lilac-colored flowers.

In September 2011, 'NE-5331' and 'NJ-1174A' were crossed and a population of F1 plants were created. The F1 plants were evaluated in a field in Misato, Japan in an open-field trial. The criteria for plant selection included compact growth habit, vigorous root system, and good flowering ability. At the completion of the trial, a single selection was made based on the above criteria and was given the experimental name 'M2013-425'. From June to August 2013, 'M2013-425' was evaluated in an open-field trial in Misato, Japan. Shoot-tip cuttings of the variety were shipped to Salinas, Calif., where the plants were propagated and evaluated for stability of traits. 'M2013-425' was subsequently named 'SAKIMP042'. 'SAKIMP042' was found to reproduce true to type in successive generations of asexual propagation via vegetative shoot-tip cuttings in Salinas, Calif.

SUMMARY

The following are the most outstanding and distinguishing characteristics of this new variety when grown under normal horticultural practices in Salinas, Calif.

1. Light coral-pink flowers; and
2. Green leaves.

DESCRIPTION OF THE PHOTOGRAPHS

This *Impatiens* plant is illustrated by the accompanying photographs which show the plant's overall plant habit including form, foliage, and flowers. The photographs are of a plant grown in Salinas, Calif. under greenhouse conditions. The colors shown are as true as can be reasonably obtained by conventional photographic procedures.

DESCRIPTION OF THE NEW VARIETY

Figure 1:
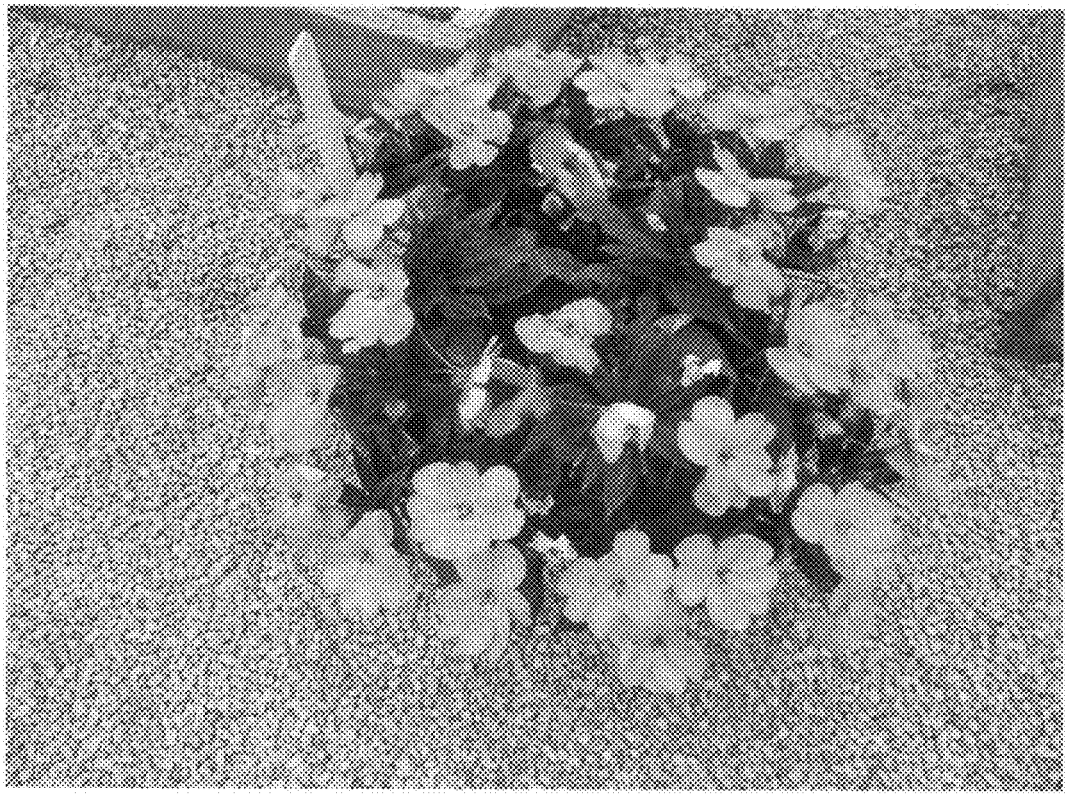
FIG. 1 shows the overall plant habit of the plant grown in a pot.
Figure 2:
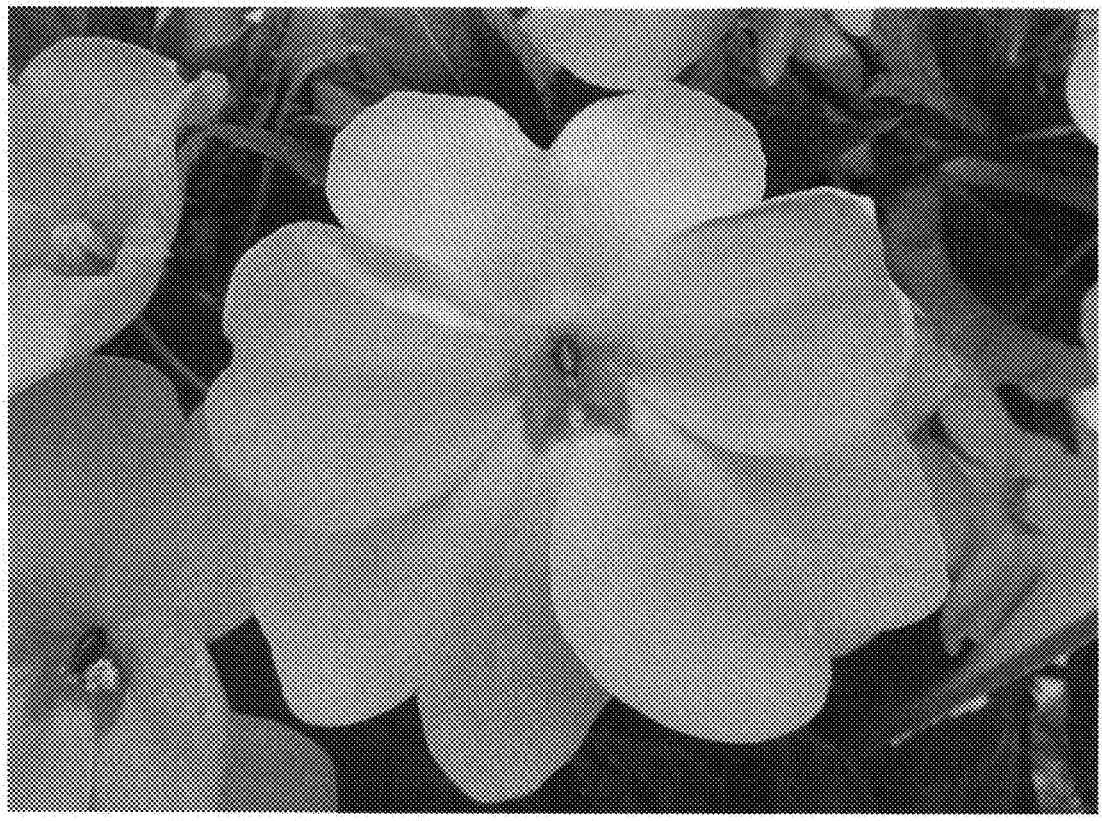
FIG. 2 shows a close-up of the mature inflorescence of the plant.

The following detailed descriptions set forth the distinctive characteristics of 'SAKIMP042'. Data was obtained from plants grown about 3-months from propagation by terminal cuttings in Salinas, Calif. under greenhouse conditions. Color references are to The Royal Horticultural Society of London colour chart (R.H.S.), $4^{th}$ edition (2001). Anatomic labels are from *The Cambridge Illustrated Glossary of Botanical Terms*, by M. Hickey and C. King, Cambridge University Press.

Classification:

*Family*.—Balsaminaceae.
*Botanical*.—*Impatiens hybrida* hort.
*Common*.—*Impatiens*.
*Designation*.—'SAKIMP042'.

Growth:

*Environmental conditions for plant growth*.—The terminal 1.0 to 1.5 inches of an actively growing stem was excised. The vegetative cuttings were propagated for five to six weeks. The base of the cuttings were dipped for 1 to 2 seconds in a 1:9 solution of DIP 'N GROW (1 solution: 9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed. Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Plants were fertilized every 2-3 days, 2 times in consecutive applications and then given one clear water application. Pots were top-dressed with a dry, slow release fertilizer containing 20% nitrogen, 10% phosphorus and 18% potassium. The typical average air temperature was 24° C.

Parentage:

*Female parent*.—The proprietary *Impatiens* variety 'NE-5331' (unpatented).

*Male parent*.—The proprietary *Impatiens* variety 'NJ-1174A' (unpatented).

Plant description:

*Habit*.—Compact.

*Life cycle*.—Annual.

*Height*.—18.5 cm from soil line to the top of the foliage.

*Spread*.—43.0 cm.

*Number of branches per plant*.—6 total with 3 main branches.

*Length of branches*.—5.0 mm from the soil line to the first node, 4.5 cm total.

*Diameter of branches*.—1.3 cm for the main branch and 1.0 cm for the other secondary branches.

*Color of branches*.—Closet to but darker than RHS 183A (Greyed-purple).

*Time to produce a rooted cutting*.—About 4 weeks.

*Time to bloom from propagation*.—6 to 8 weeks.

*Flowering requirements*.—Will flower so long as temperature is above 5° C.

*Temperature tolerances*.—Plants observed to continue flowering in a temperature range of 5° C. to 36° C.

Stems:

*Color*.—Closest to RHS 183A (Greyed-purple).

*Anthocyanin color*.—RHS 183A (Greyed-purple).

*Pubescence*.—Very slight.

*Pubescence color*.—RHS 155A (White).

*Description*.—Strong; circular in cross-section; shiny, with very slight pubescence.

*Length*.—4.0 cm to 4.5 cm from the first node to the second node; 9.0 cm to 12.5 cm total.

*Diameter*.—5.0 mm to 8.0 mm.

*Internode length*.—4.5 cm.

Leaves:

*Arrangement*.—Whorled with up to 5 leaves per node, opposite if only two leaves at one node.

*Shape*.—Lanceolate, curled.

*Apex*.—Acuminate.

*Base*.—Shortly attenuate.

*Margin*.—Serrate.

*Surface appearance*.—Dull, waxy.

*Length*.—8.6 cm.

*Width*.—3.3 cm.

*Color*.—Upper surface: Closest to but darker than RHS 147A (Yellow-green). Lower surface: Closest to but darker than RHS 148B (Yellow-green).

*Variegation*.—Absent.

*Fragrance*.—Absent.

*Pubescence*.—Absent.

*Petiole*.—Length: 9.0 mm. Diameter: 2.0 mm. Color: Closest to RHS 145C (Yellow-green). Texture: Smooth, glabrous. Venation pattern: Pinnate. Venation color: Upper surface: Closest to RHS 183A (Greyed-purple). Lower surface: Closest to RHS 183D (Greyed-purple).

Flower buds:

*Surface texture*.—Glabrous.

*Length*.—2.2 cm.

*Diameter*.—1.5 cm.

*Shape*.—Deltoid; longitudinal in cross-section.

*Color*.—Closest to RHS 52B (Red) with RHS 183A (Greyed-purple) at the edge.

Flowers:

*Inflorescence type*.—Single flower with spur.

*Number of flowers per node*.—1 to 3 in bloom at one time; about 10 flower buds.

*Number of flowers per plant*.—Approximately 65 in bloom.

*Lastingness of individual blooms on the plants*.—14 days.

Corolla:

*Shape*.—Roughly circular with 5 radial petals.

*Diameter*.—6.8 cm.

*Depth*.—1.0 cm.

*Petals*.—Texture (both surfaces): Glabrous. Length: 3.8 cm. Width: 4.0 cm. Shape: Obcordate. Apex: Emarginate (cleaved). Base: Attenuate. Margin: Entire. Color: Upper surface: Closest to but brighter than RHS 52A (Red). Lower surface: Closest to RHS 58D (Red-purple). Eye zone: Closest to but brighter than RHS 60A (Red-purple).

Calyx:

*Sepal shape*.—Lanceolate.

*Sepal apex*.—Caudate.

*Sepal base*.—Subcordate.

*Sepal margin*.—Entire.

*Sepal texture* (*both surfaces*).—Glabrous.

*Sepal number per flower*.—2.

*Sepal color*.—Upper surface: RHS 183A (Greyed-purple) with very slight RHS 142B (Green). Lower surface: Closest to RHS 142B (Green).

*Sepal length*.—1.5 cm.

*Sepal diameter*.—7.0 mm.

Spur:

*Color*.—Closest to RHS 60B (Red-purple) with RHS N77A (Purple) at the tip; RHS 62D (Red-purple) at the base with slight RHS 147B (Yellow-green) at the tip of the base.

*Shape*.—Tubular and curved downward.

*Length*.—6.7 cm.

*Diameter*.—1.0 mm to 2.0 mm.

Peduncle:

*Length*.—4.8 cm.

*Color*.—RHS 183B (Greyed-purple).

*Diameter*.—2.0 mm.

*Texture*.—Smooth, glabrous.

Reproductive organs:

*Stamens*.—Form: Fused, split into 4 lobes. Number per flower: 5. Filament form: Free. Anther length: 6.0 mm. Anther color: Closest to RHS 58A but slightly transparent. Pollen amount: Abundant. Pollen description: Powdery. Pollen color: RHS 155B (White).

*Pistil*.—Number per flower: 1. Stigma color: RHS 156B (Greyed-white). Style color: RHS N77A (Purple) with RHS 144A (Yellow-green). Ovary arrangement: Parietal. Ovary interior color: RHS 145B (Yellow-green).

*Seed production*.—Not observed.

Disease and insect resistance: No particular resistance or susceptibility observed.

COMPARISON WITH PARENTAL LINES AND KNOWN VARIETY

'SAKIMP042' is a new and unique variety of *Impatiens* having a compact growth habit, strong root system, and good flowering ability. 'SAKIMP042' is distinguished from its parents as shown in Table 1.

TABLE 1

Comparison with Parental Lines

| Characteristic | 'SAKIMP042' | Female Parent 'NE-5331' | Male Parent 'NJ-1174A' |
|---|---|---|---|
| Flower color | Coral-pink | Salmon-orange | Lilac |
| Plant growth habit | Compact | Mounding | Mounding |

'SAKIMP042' is a new and unique variety of *Impatiens* having a compact growth habit, strong root system, and good flowering ability. When 'SAKIMP042' is compared to the commercial *Impatiens* variety 'SAKIMP013' (U.S. Plant Pat. No. 19,957), the following differences as described in Table 2.

TABLE 2

Comparison with Similar Variety

| Characteristic | 'SAKIMP042' | 'SAKIMP013' |
|---|---|---|
| Petal color, upper surface | Closest to but brighter than RHS 52A (Red) | RHS 65C (Red-purple) |
| Petal color, lower surface | Closest to RHS 58D (Red-purple) | RHS 65C (Red-purple) |
| Spur color | Closest to RHS 60B (Red-purple) with RHS N77A (Purple) at the tip; Also RHS 62D at the base with a slight RHS 147B (Yellow-green) at the tip of the base | RHS 65D (Red-purple) |

We claim:

1. A new and distinct variety of New Guinea *Impatiens* plant named 'SAKIMP042' as described and illustrated herein.

* * * * *